United States Patent [19]

Nysted

[11] 4,013,643

[45] Mar. 22, 1977

[54] N,N-DISUBSTITUTED 2,3-DIPHENYLALLYLAMINES

[75] Inventor: Leonard N. Nysted, Highland Park, Ill.

[73] Assignee: G. D. Searle & Co., Chicago, Ill.

[22] Filed: July 25, 1975

[21] Appl. No.: 599,311

Related U.S. Application Data

[63] Continuation of Ser. No. 417,289, Nov. 19, 1973, abandoned, which is a continuation-in-part of Ser. No. 215,923, Jan. 6, 1972, abandoned.

[52] U.S. Cl. ............... 260/240 K; 260/240 CA; 260/240 R; 260/562 P; 260/567.6 M; 260/570.5 R; 424/251; 424/258; 424/263; 424/267; 424/274; 424/324; 424/329; 424/330

[51] Int. Cl.$^2$ ............... C07D 239/06; C07C 87/29

[58] Field of Search ............ 260/240 K, 567.6 M, 260/240 CA, 570.5 R, 562 P

[56] References Cited

UNITED STATES PATENTS

| | | | |
|---|---|---|---|
| 2,485,662 | 10/1949 | Rohrmann | 260/247 |
| 3,422,153 | 1/1969 | Mills et al. | 260/570.5 R |

OTHER PUBLICATIONS

Jones et al. J. Med. Chem. 14 (1971) pp. 161–164.
Shapiro Chem. Abst. 46 3056(d).
Fuks et al. Chem Ber. 103 (1970) pp. 564, 565, 571.

*Primary Examiner*—Arthur P. Demers
*Attorney, Agent, or Firm*—John M. Brown; John A. Dhuey

[57] ABSTRACT

The above-captioned compounds are produced from optionally substituted benzoin compounds by sequential reactions with trizincbismethylene dibromide, phosphorous trichloride and an appropriately substituted amine. The instant compounds are valuable as pharmacological agents as is evidenced by their antimicrobial, anti-arrhythmic, pepsin-inhibitory and antihypertensive activity.

5 Claims, No Drawings

N,N-DISUBSTITUTED 2,3-DIPHENYLALLYLAMINES

This is a continuation of application Ser. No. 417,289, filed Nov. 19, 1973, now abandoned, which is a continuation-in-part of application Ser. No. 215,923, filed Jan. 6, 1972, now abandoned.

The present invention is concerned with diphenylallylamines. In particular, it is concerned with N,N-disubstituted 2,3-diphenylallylamines and derivatives of the formula

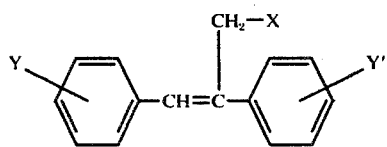

wherein X is an amino, (lower alkyl)amino, di(loweralkyl) amino, di[(lower alkoxy)lower alkyl]amino, aralkylamino radical or an optionally-substituted heterocyclic amino radical, e.g. morpholino, piperidino, pyrolyl, 1,2-dihydropyrid-1-yl, 1,2-dihydroquinol-1-yl, 1,2-dihydroisoquinol-1-yl, α-,β-, or γ-1,2-dihydropicol-1-yl, 3-chloro-1,2-dihydropyrid-1-yl, (lower alkanoyl)-1,2-dihydropyrid-1-yls such as 3-acetyl-1,2-dihydropyrid-1-yl and 1,2-dihydropyrimidin-1-yl radicals such as 4-amino-2-oxo-1,2-dihydropyrimidin-1-yl and radicals of the formula

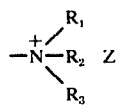

wherein $R_1$, $R_2$ and $R_3$ are hydrogen, lower alkyl or aralkyl radicals or radicals of the above formula wherein $NR_1R_2R_3$ represents an optionally-substituted heterocyclic amine such as pyrimidine, morpholine, pyridine, quinoline, isoquinoline, α-picoline, β-picoline, γ-picoline, 3-chloropyridine, 2,3- and 4-carboxypyridine, and (lower alkanoyl)pyridines such as 3-acetylpyridine or heterocycloaliphatic amines such as N-alkylmorpholines, N-alkylpiperidines and N-alkylpyrolidenes, $Z^-$ is a pharmaceutically acceptable ion such as halogen, citrate, oxalate, tartrate, maleate, ascorbate, gluconate, lactate, succinate, phosphate or sulfate and Y and Y' represent hydrogen, lower alkoxy, halogen or acetamido radicals with the provision that when X is amino, Y and Y' are hydrogen, halogen or acetamido radicals. The quaternary ammonium salts are represented by the above formula when $R_1$, $R_2$ and $R_3$ are lower alkyl or aralkyl radicals.

It is understood that the phenyl groups may be singly or multiply substituted and that the mixed compounds, wherein Y and Y' are not the same, are also represented.

Preferred among the compounds described above are the quaternary ammonium salts and the compounds in which X is an amino, di(lower alkyl)amino or di[(lower alkoxy)lower alkyl]amino radical. Especially preferred are the quaternary ammonium salts and the compounds wherein X is a di(lower alkyl)amino radical, with the quaternary ammonium salts being most especially preferred.

The lower alkyl radicals represented by the above formula are methyl, ethyl, propyl, butyl, pentyl, hexyl, heptyl and the branched-chain isomers thereof and the aralkyl radicals are benzyl and phenethyl. The lower alkoxy radicals represented contain up to 7 carbon atoms and are illustrated by methoxy, ethoxy, propoxy and isopropoxy. The halogen atoms represented are illustrated by fluorine, chlorine, iodine and bromine radicals.

The novel compounds of the this invention are prepared from the appropriately substituted benzoin compounds which are represented by the following structural formula

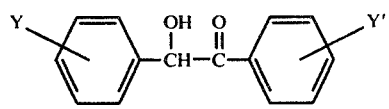

where Y and Y' are halogen, lower alkoxy, acetamido or hydrogen radicals. It is understood that the phenyl groups may be singly or multiply substituted and that the mixed benzoin compounds, wherein Y and Y' are not the same, are also represented. The manufacturing process conveniently begins with the methylenation of the appropriately substituted benzoin with trizincbismethylene dibromide which is prepared from dry zinc and methylene bromide. The trizincbismethylene dibromide reagent is employed in situ and the optionally substituted benzoin compound is added to it. Typical of this step is the addition of benzoin to a preparation of trizincbismethylene dibromide in tetrahydrofuran to produce the methylenated benzoin derivative, 1,2-diphenyl-2-propen-1-ol. The methylenated benzoin derivatives then are allowed to react with a phosphorous trihalide in an inert solvent to produce the 2,3-diphenylallyl halide compounds. For example, when 1,2-diphenyl-2-propen-1-ol is allowed to react with phosphorous trichloride in methylene chloride, there is afforded 2,3-diphenylallyl chloride. Reaction of the allyl chlorides with an appropriately substituted amine then produces the compounds of the present invention. In that manner, when 2,3-diphenylallyl chloride is treated with diethylamine, ammonia or morpholine there is produced, respectively, N,N-diethyl-2,3-diphenylallamine, 2,3-diphenylallylamine and N-(2,3-diphenylallyl)morpholine. Likewise when bis-trimethylsilylcytosine and bisethoxyethylamine are allowed to react with the 2,3-diphenylallylchloride, there are produced, respectively, 1-(2,3-diphenylallyl)-4-amino-2-oxo-1,2-dihydro-pyrimidine and N,N-diethoxyethyl-2,3-diphenylallylamine citrate.

The quaternary ammonium salts may be prepared from the tertiary amines by reaction with an alkyl or aralkyl halide. Thus, for example, when N,N-diethyl-2,3-diphenylallylamine is allowed to react with methylene bromide, there is produced N,N-diethyl-N-methyl-2,3-diphenylallylammonium bromide.

The acid salts of addition are prepared by contacting the amines with a mineral acid such as hydrochloric acid or an organic acid such as citric or oxalic acid or acids of the aforementioned salts. Typically, 2,3-diphenylallyl chloride is allowed to react with bisethoxyethylamine and the product is contacted with citric acid to afford N,N-diethoxyethyl-2,3-diphenylallylamine citrate.

The instant compounds are useful as pharmacological agents. For example, they possess anti-microbial, anti-arrhythmic, pepsin-inhibitory and anti-hypertensive activity. The pepsin-inhibitory activity is shown by an assay described in U.S. Pat. No. 3,509,137. The anti-arrhythmic activity of the instant compounds is demonstrated in an assay described in U.S. Pat. No. 3,573,288 and also in the following assay:

The antiarrhythmic utility of the instant compounds is evident from the results of a standardized test for their capacity to slow the ventricular tachycardia induced by aconitine in the isolated rabbit heart. The procedure is essentially that described by Lucchesi [J. Pharmacol. Exp. Therap., 137, 291 (1962)], modified in certain particulars as follows: Hearts are obtained from adult albino rabbits of either sex and perfused in apparatus modeled after that devised by Anderson and Craver [J. Pharmacol. Exp. Therap., 93, 135 (1948)]. Composition of the perfusion solution is the same as Lucchesi's, but the volume is increased to 200 ml. and the temperature lowered to 28°. Aconitine (ordinarily as the nitrate) is administered as soon as the heart beat is regular and the EKG pattern normal, the dose being so selected as to at least double the rate. Typically, 0.05 ml. of 0.1% aconitine nitrate in physiological saline is injected. EKG's are recorded at 5 minute intervals after onset of ventricular tachycardia until two successive readings show stabilization of the rate. Perfusate collected during this time is discarded and replaced with fresh solution q.s. 200 ml. Promptly following stabilization, 2 mg. of compound dissolved or suspended in 1 ml. of physiological saline, is mixed with the perfusion solution. Ten minutes later a like amount is introduced, followed after a further 10 minutes by double the first amount. Final concentration of compound in the perfusion solution is thus 40 mg. per l. Recording of EKG's is continued at 5 minute intervals throughout this time and for 10 minutes thereafter. A compound is considered antiarrhythmic if, at any time during the 30 minutes immediately following initial administration in at least half of a minimum of two tests, it reduces by 50% or more the rate recorded ten minutes after onset of tachycardia.

The anti-arrhythmic activity of the instant compounds also is demonstrated by their ability to reverse ouabain induced unifocal or multifocal ventricular tachycardia as shown in the following assay based on a procedure described by B. R. Lucchesi and H. F. Hardman, J. Pharmacol. and Exp. Ther., 132, 372 (1961).

Male dogs are anesthetized with sodium pentobarbital (32.5 mg./kg., intravenously) and prepared with indwelling arterial cannula for blood pressure recording and a venous catheter for drug administration. The standard limb Lead II electrocardiogram is recorded. Then 40 mcg./kg. of ouabain is injected over a 5 minute period, followed by 20 mcg./kg. after 30 minutes and 10 mcg./kg. every 15 minutes thereafter until a self-sustaining (> 15 minutes) ventricular tachycardia is produced. Test compound then is administered intravenously in 5 mg./kg. doses every 10 minutes until normal sinus rhythm occurs or a total of 20 mg./kg. is administered. A compound is considered active if normal sinus rhythm occurs in at least half of the test animals at a total dose of ≦ 20 mg./kg.

The present compounds also are useful as anti-hypertensive agents. This utility is demonstrated by the following test procedure which makes use of the fact that chronic administration of desoxycorticosterone acetate induces a self-sustaining hypertension that is similar in many respects to essential hypertension in man (D. N. Green et al., *American Journal of Physiology*, 170, 94, 1952). In this test, 50-g. male Charles River rats are implanted with a 20 mg. wax pellet containing 10 mg. of desoxycorticosterone acetate. After 5 weeks, their systolic blood pressures are measured electrosphygmographically on the tail artery. The following day, groups of 5 rats are then given 60 mpk. of test compound intragastrically. Four hours later, the blood pressures are again measured and the decrease in pressure from control day is calculated and compared with concurrent controls. A compound is considered active if it produces a significant decrease in systolic blood pressure.

The instant compounds are also anti-microbial agents as evidenced by their anti-bacterial activity, in particular against *Bacillus subtilis, Escherichia coli, Salmonella paratyphi* A and *Erwinia sp.*, their anti-protozoal activity, in particular against *Trichomonas vaginalis*, their anthelmintic activity, specifically against *Turbatrix aceti*, their anti-fungal activity, specifically against *Verticillium albo-atrum, Trichophyten mentagrophytes* and *Candida albicans*, and their anti-algal activity, in particular against *Chlorella vulgaris*.

The assay used to detect the anti-bacterial activity of the instant compounds is described as follows:

A nutrient broth (manufactured by Baltimore Biological Laboratories or Difco) is prepared at twice the concentration recommended by the manufacturer, sterilized, then inoculated with 2% (by volume) of a culture of *Bacillus subtilis, Escherichia coli, Salmonella paratyphi* A or *Erwinia* sp. Meanwhile, the test compound is heated in sterile distilled water at a concentration of 2000 mcg./ml. and a temperature of 80° C. for 20 minutes. An equivolume mixture of this compound preparation and the inoculated broth is incubated aerobically at 37° C., then is examined grossly for growth of the test organism. The incubation period is 24–48 hours for *Erwinia* sp. and 20–24 hours for the other three organisms. If growth of the test organism is observed, the compound is considered inactive. If no such growth is observed, the incubated mixture is serially diluted and mixed with an inoculated broth of the same composition as before excepting that the concentration is halved and 1% (by volume) of the culture instead of 2% is incorporated. Amounts of the latter broth added are such that concentrations of 100, 10 and 1 mcg. of compound per ml. result. The mixtures thus obtained are incubated as before, then examined grossly for growth of the test organism. Potency is expressed as the minimum concentration at which no growth of test organism is discernible. Controls are provided by concurrent incubations identical with the foregoing except for the absence of the test compound.

The anti-protozoal activity of the compounds of the present invention is determined by an assay utilizing *Trichomonas vaginalis*. In that assay, 80 volumes of a modified Diamond medium prepared by mixing 1200 parts of trypticase (Baltimore Biological Laboratories), 600 parts of yeast extract, (Difco), 300 parts of maltose, 60 parts of L-cysteine hydrochloride, 12 parts of L-ascorbic acid, 48 parts of dibasic potassium phosphate, 48 parts of monobasic potassium phosphate and 27,000 parts of distilled water; adjusting the pH to 6.8 with aqueous 4% sodium hydroxide; incorporating 30 parts of agar (Baltimore Biological Laboratories); boiling for 1 minute to dissolve the agar; and sterilizing is diluted with 20 volumes of sterile Dubos medium serum. The resulting medium is inoculated with 2% (by volume) of either a 48-hour or 72-hour culture of *Trichomonas vaginalis*. Meanwhile, the test compound is heated in sterile distilled water at a concentration of 2000 mcg./ml. and a temperature of 80° C. for 20 minutes. An equivolume mixture of this compound preparation and the inoculated medium is incubated anaerobically at 37° C. for 48 hours, then is examined microscopically for the presence of motile trichomonads. If any are observed, the compound is considered inactive. If no motile trichomonads are observed, the incubated mixture is serially diluted and mixed with an inoculated medium of the same composition as that described above expecting that 54,000 parts of distilled water instead of 27,000 parts and 1% (by volume) of the culture instead of 2% are incorporated. Amounts of the latter medium added are such that concentrations of 1000, 10 and 1 mcg. of compound per ml. result. The mixtures thus obtained are incubated as before and then examined microscopically for motile trichomonads. Potency is expressed as the minimum concentration at which no motile trichomonads are discernible. Controls are provided by concurrent incubations identical with the foregoing except for the absence of the test compound.

Evidence for the anthelmintic activity of the instant compounds is provided by an assay utilizing *Turbatrix aceti*, a representative menatode. In this assay, the test compound is heated in sterile distilled water at a concentration of 2000 mcg./ml. and a temperature of 80° C. for 20 minutes, whereupon an equivolume mixture of this compound preparation and a washed aqueous suspension of *Turbatrix aceti* containing approximately 2000 nematodes per ml. is incubated anaerobically at room temperature for 48 hours and then examined grossly for the presence of motile nematodes. If any are observed, the compound is considered inactive. If no motile nematodes are observed, the incubated mixture is serially diluted and mixed with a freshly prepared and washed aqueous suspension of *Turbatrix aceti* containing approximately 1000 nematodes per ml. in amounts such that concentrations of 100, 10 and 1 mcg. of compound per ml. result. The mixtures thus obtained are incubated as before and then examined grossly for the presence of motile nematodes. Potency is expressed as the minumum concentration at which no motile nematodes are discernible. Controls are provided by concurrent incubations identical with the foregoing except for absence of the test compound.

Confirmation of the anti-fungal activity of the compounds of this invention is afforded by an assay utilizing either *Trichophyton mentagrophytes*, *Verticillium alboatrum* or *Candida albicans*. In this assay, the test compound is dissolved or suspended in melted Sabouraud agar and is held at 80° C. for 20 minutes. Dilutions are made from this preparation in melted Sabouraud agar in order to give concentrations of the test substance of 1000, 100, 10 and 1 mcg./ml. in the agar. The agar is permitted to cool and solidify and is then surface inoculated with a suspension of spores of *Verticillium alboatrum Trichophyton mentagrophytes* or *Candida albicans*. The inoculated media are incubated at room temperature, those containing *Candida albicans* for about 48 hours and those containing *Verticillium alboatrum* or *Trichophyton mentagrophytes* for 6–7 days, then are examined grossly for the presence or absence of growth of the test organism. Control preparations lacking the test compound are employed for comparative purposes. Activity is reported as mcg. of the compound/ml. of agar which completely prevents visible growth of the test organism.

The anti-algal property of the instant compounds is demonstrated by their activity in the following assay:

Sterile Bristol medium of two times the normal concentration in inoculated with an aqueous suspension of *Chlorella vulgaris* and 0.5 ml. of that inoculated medium is mixed with 0.5 ml. of a stock solution or suspension of the test compound in sterile distilled water prepared at a concentration of 2 mg./ml. Serial dilutions are made using single strength Bristol medium, thus affording mixtures having concentrations of 1000, 100, 10 and 1 mcg./ml. Those inoculated media are incubated at room temperature under artificial light for 4–5 days, then are examined macroscopically for the presence or absence of growth of the organism. The activity of the test compound is reported as the concentration at which no algal growth is observed. A control mixture identical save for omission of the test compound is prepared for comparison purposes.

The invention will appear more fully from the examples which follow. They are not to be construed as limiting the invention either in spirit or in scope as many modifications both in materials and methods will be apparent to one skilled in the art. In the examples which follow temperatures are given in degrees Centigrade and quantities of material in parts by weight unless noted otherwise.

EXAMPLE 1

To a stirred suspension of 75 parts of zinc in 59.3 parts of methanol and 26.2 parts of acetic acid, under a nitrogen atmosphere, is added 5 parts of hydrochloric acid dissolved in 19.6 parts of isopropanol. That mixture is heated to reflux while stirring rapidly. Then the heat is removed and the stirring is stopped and the solvent removed by suction with a sintered suction tube. The zinc then is washed by successive addition, brief stirring and removal by suction of 39.6 parts of methanol, 66.8 parts of methylene chloride and 74.5 parts of chloroform. After drying the zinc under nitrogen on a steam bath at 100°, the dry zinc is covered with 110 parts of tetrahydrofuran and a solution of 70 parts of methylene dibromide diluted with 66.6 parts of tetrahydrofuran is added while stirring and refluxing over a 15 minute period. The mixture is allowed to reflux for 20 hours and, after that time period, the mixture is cooled to −10°. Then 21.0 parts of benzoin is added rapidly and the reaction is allowed to warm slowly to room temperature and stirred for 24 hours. The reaction mixture is cooled in a cold water bath, and a 1:1 acetic acid-water mixture is added cautiously. The excess zinc then is removed by filtration and the filtrate is steam distilled for 15 minutes to remove the solvent. The solid, crystalline 1,2-diphenyl-2-propen-1-ol which remains displays maxima in the nuclear magnetic resonance spectrum at about 124, 324, 336, 430 and 434 Hertz.

EXAMPLE 2

A solution comprised of 14 parts of 1,2-diphenyl-2-propen-1-ol and 24.3 parts of methylene chloride is added dropwise to a solution comprised of 12.6 parts of phosphorous trichloride and 30.4 parts of methylene chloride at a temperature of −15°. That reaction mixture is allowed to warm to 0° over a 3 hour period.

Then ice is added while stirring rapidly and the oil which separates is extracted with ethyl ether. The ethereal extracts are washed with water and then with 10% potassium bicarbonate solution. After drying over anhydrous sodium sulfate, the solution is reduced to an oil by evaporating the solvent under a nitrogen stream and reduced pressure to yield pure 2,3-diphenylallyl chloride.

EXAMPLE 3

A solution consisting of 4 parts of 2,3-diphenylallyl chloride dissolved in 7.12 parts of diethylamine is allowed to stand at 65° for about 24 hours. Then the excess diethylamine is removed under nitrogen and the oil and solid which remain are covered with n-hexane. The solid is separated by filtration and the filtrate is acidified by adding isopropanolic hydrochloric acid. The oil which separates is then isolated by decantation and crystallized from isopropanol-ethyl ether to yield pure N,N-diethyl-2,3-diphenylallylamine hydrochloride, melting at about 190° and displaying maxima in the nuclear magnetic resonance spectrum at about 70, 76, 82, 162–190, 242, 246 and 422–436 Hertz. That compound is represented by the following structural formula

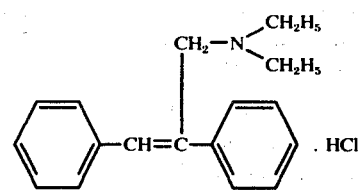

EXAMPLE 4

Ammonia under pressure is added to a solution of 4 parts of 2,3-diphenylallyl chloride in 44 parts of benzene at 70° for 24 hours. After that time, the solid is separated by filtration and the benzene solution is reduced to an oil under reduced pressure. The oil is dissolved in isopropanolic hydrochloric acid and then diluted with ethyl ether to precipitate a solid. The solid is collected by filtration and dried to yield pure 2,3-diphenylallylamine hydrochloride, displaying nuclear magnetic resonance maxima at about 240, 241, 413, 426 and 442 Hertz and represented by the following structural formula

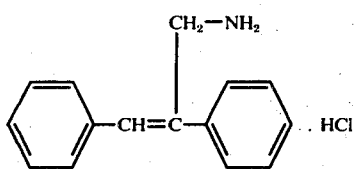

EXAMPLE 5

When an equivalent quantity of morpholine is substituted in the procedure of Example 3, there is produced N-(2,3-diphenylallyl)morpholine hydrochloride, displaying nuclear magnetic resonance peaks at about 190, 240–242, 258, 428 and 440 Hertz and structurally represented by the following formula

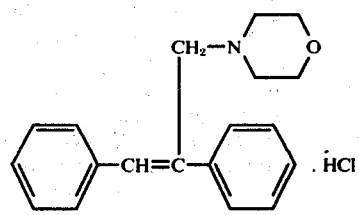

EXAMPLE 6

By substituting an equivalent quantity of dimethylamine in the procedure of Example 3 and otherwise following the procedure of Example 3, there is produced N,N-dimethyl-2,3-diphenylallylamine.

EXAMPLE 7

When an equivalent quantity of ethylamine is substituted in the procedure of Example 3, there is afforded N-ethyl-2,3-diphenylallylamine.

EXAMPLE 8

Substitution of an equivalent quantity of methylamine in the procedure of Example 3 produces N-methyl-2,3-diphenylallylamine.

EXAMPLE 9

When the procedures of Examples 1, 2 and 3 are applied to the following compounds:
 4,4'-dimethoxybenzoin,
 3,3',4,4',5,5'-hexamethoxybenzoin,
 4,4'-dichlorobenzoin,
 3,3',4,4',5,5'-hexachlorobenzoin,
 4,4'-dibromobenzoin,
 4,4'-diacetamidobenzoin,
 4,4'-diethoxybenzoin,
 3,4,5-trichlorobenzoin,
 3,3'-dimethoxybenzoin, and
 2,2'-dimethoxybenzoin,
there is produced, respectively,
 N,N-diphenyl-2,3-di(4-methoxyphenyl)allylamine,
 N,N-diethyl-2,3-di(3,4,5-trimethoxyphenyl)allylamine,
 N,N-diethyl-2,3-di(4-chlorophenyl)allylamine,
 N,N-diethyl-2,3-di(3,4,5-trichlorophenyl)allylamine,
 N,N-diethyl-2,3-di(4-bromophenyl)allylamine,
 N,N-diethyl-2,3-di(4-acetamidophenyl)allylamine,
 N,N-diethyl-2,3-di(4-ethoxyphenyl)allylamine,
 N,N-diethyl-2-(3,4,5-triethoxyphenyl)-3-phenylallylamine,
 N,N-diethyl-2,3-di(3-methoxyphenyl)allylamine, and
 N,N-diethyl-2,3-di(2-methoxyphenyl)allylamine.

EXAMPLE 10

By treating the following compounds:
 4,4'-dichlorobenzoin,
 3,3',4,4',5,5'-hexachlorobenzoin,
 4,4'-dibromobenzoin, and
 3,4,5-trichlorobenzoin
according to the procedure described in Examples 1, 2 and 4, there is obtained, respectively,
 2,3-di(4-dichlorophenyl)allylamine,
 2,3-di(3,4,5-trichlorophenyl)allylamine,
 2,3-di(4-bromophenyl) allylamine, and
 2-(3,4,5-trichlorophenyl)-3-phenylallylamine.

EXAMPLE 11

3 Parts of methylene bromide is bubbled into a solution of 5 parts of N,N-diethyl-2,3-diphenylallylamine dissolved in 19.8 parts of acetone. Then the reaction container is sealed and allowed to stand at room temperature for 24 hours. After that time, the solid which crystallizes is separated by filtration, washed with acetone and dried under reduced pressure to yield, N,N-diethyl-N-methyl-2,3-diphenylallylammonium bromide. That compound displays absorption in the ultraviolet spectrum at about 225 and 273 millimicrons and maxima in the nuclear magnetic resonance spectrum at about 72, 78, 84, 190, 201, 208, 216, 223, 296, 424, 426, 442 and 453 Hertz. It is represented by the following structural formula

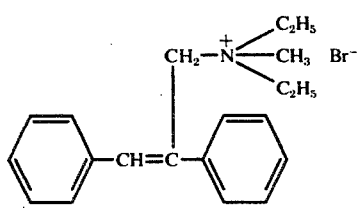

EXAMPLE 12

A solution of 10 parts of 2,3-diphenylallyl chloride in 43.9 parts of benzene is treated with 20 parts of bis-trimethylsilylcytosine under a nitrogen atmosphere and then the reaction container is sealed and maintained at a temperature of 65° for 120 hours. The solid which forms is collected by filtration, washed with benzene and recrystallized from a 1:1 acetic acid-water mixture to yield 1-(2,3-diphenylallyl)-4-amino-2-oxo-1,2-dihydro-pyrimidine. That product displays nuclear magnetic resonance maxima at about 293, 405, 425, 437, 453 and 461 Hertz and is represented structurally by the following formula

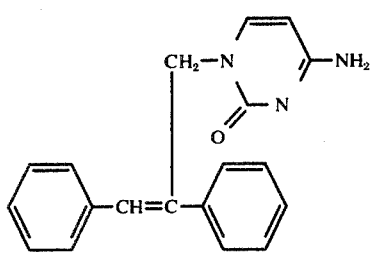

EXAMPLE 13

5 Parts of 2,3-diphenylallyl chloride is dispersed in 10 parts of bisethoxyethylamine and maintained at 60° for 72 hours. The mixture is filtered and the filtrate is reduced to an oil under reduced pressure. Then the oil is dissolved in 90 parts of ethyl acetate and 200 parts by volume of a saturated citric acid monohydrate in ethyl acetate solution is added to the ethyl acetate solution. The oil which separates is crystallized by swirling the solution and the crystalline solid is recovered by filtration. Then the solid is washed with ethyl acetate and dried under reduced pressure to yield N,N-diethoxyethyl-2,3-diphenylallylamine citrate, exhibiting absorption bands in the ultraviolet spectrum at about 222 and 265 millimicrons and nuclear magnetic resonance peaks at about 58, 65, 72, 186, 203, 209, 215, 232, 277, 433, 439 and 447 Hertz. The product is represented by the following structural formula

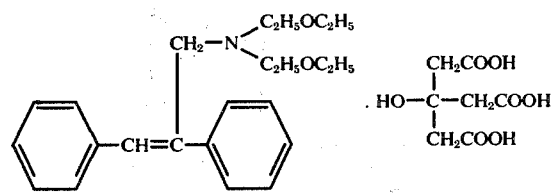

EXAMPLE 14

By substituting equivalent quantities of 2,2'-dimethoxybenzoin, 3,3-dimethoxybenzoin and 4,4'-dimethoxybenzoin into the procedure of Example 1 and subsequently following the procedure of Example 2, there is afforded, respectively, 2,3-di(2-methoxyphenyl)allyl chloride, 2,3-di(3-methoxyphenyl)allyl chloride and 2,3-di(4-methoxyphenyl)allyl chloride.

EXAMPLE 15

By substituting equivalent quantities of 2,3-di(3-methoxyphenyl)allyl chloride and dimethylamine in the procedure of Example 3, there is produced N,N-dimethyl-2,3-di(3-methoxyphenyl)allylamine hydrochloride.

EXAMPLE 16

When equivalent quantities of 2,3-di(4-methoxyphenyl)allyl chloride and dimethylamine are substituted in the procedure of Example 3, there is produced N,N-dimethyl-2,3-di(4-methoxyphenyl)allylamine hydrochloride.

EXAMPLE 17

Substitution of equivalent quantities of 2,3-di(2-methoxyphenyl)allyl chloride and dimethylamine in the procedure of Example 3 yields N,N-dimethyl-2,3-di(2-methoxyphenyl)allylamine.

EXAMPLE 18

2.2 Parts of N,N-dimethyl-2,3-di(2-methoxyphenyl)allylamine is combined with 5 parts by volume of isopropyl bromide. That mixture is allowed to stand at 65° for 21 days. Ethyl acetate is added to the solid which forms and the solid is broken and triturated. That mixture then is filtered, and the solid collected is washed with ethyl acetate and dried to afford N-isopropyl-N,N-dimethyl-2,3-di(2-methoxyphenyl)allylammonium bromide. That compound is structurally represented by the following formula

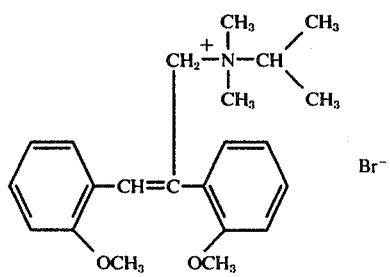

What is claimed is:

1. A compound of the formula

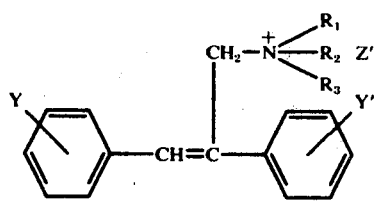

wherein Y and Y' are halogen, lower alkoxy, acetamido or hydrogen radicals, $R_1$, $R_2$ and $R_3$ are lower alkyl radicals and Z is a halogen atom.

2. The compound which is N,N-diethoxyethyl-2,3-diphenylallylamine.

3. The compound which is 1-(2,3-diphenylallyl)-4-amino-2-oxo-1,2-dihydro-pyrimidine.

4. The compound which is N,N-diethyl-N-methyl-2,3-diphenylallylammonium bromide.

5. The compound which is N-isopropyl-N,N-dimethyl-2,3-diphenylallylammonium bromide.

* * * * *

UNITED STATES PATENT AND TRADEMARK OFFICE
CERTIFICATE OF CORRECTION

PATENT NO. : 4,013,643
DATED : Mar. 22, 1977
INVENTOR(S) : Leonard N. Nysted

It is certified that error appears in the above-identified patent and that said Letters Patent are hereby corrected as shown below:

Column 1, second formula,

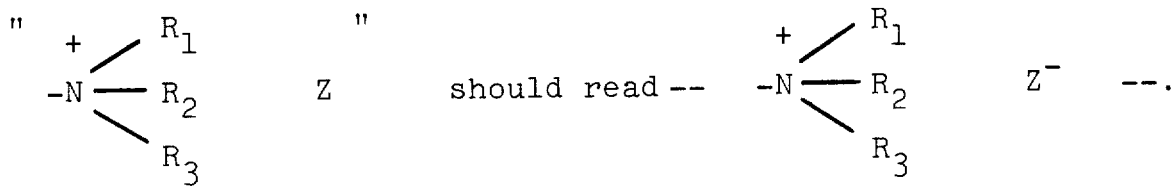

Column 5, line 15, "expecting" should read -- excepting --.

Column 6, line 8, "in" should read -- is --.

Signed and Sealed this

Twenty-fifth Day of October 1977

[SEAL]

Attest:

RUTH C. MASON
Attesting Officer

LUTRELLE F. PARKER
Acting Commissioner of Patents and Trademarks